(12) United States Patent
Yoon et al.

(10) Patent No.: US 7,654,144 B2
(45) Date of Patent: Feb. 2, 2010

(54) NONDESTRUCTIVE TESTING APPARATUS FOR BLADE ROOT OF STEAM TURBINE OF POWER PLANT

(75) Inventors: Byung Sik Yoon, Daejeon (KR); Yong Sik Kim, Daejeon (KR); Hee Jong Lee, Daejeon (KR); Se Kyoung Kim, Daejeon (KR); Seung Han Yang, Daejeon (KR)

(73) Assignee: Korea Electric Power Corporation, Seoul (KR)

( * ) Notice: Subject to any disclaimer, the term of this patent is extended or adjusted under 35 U.S.C. 154(b) by 217 days.

(21) Appl. No.: 11/955,607

(22) Filed: Dec. 13, 2007

(65) Prior Publication Data

US 2009/0151458 A1  Jun. 18, 2009

(51) Int. Cl.
  *G01N 9/24* (2006.01)
(52) U.S. Cl. .............................. 73/639; 73/593; 73/627; 73/646
(58) Field of Classification Search .................... 73/639, 73/646, 649, 593, 623, 627, 749, 779
  See application file for complete search history.

(56) References Cited

U.S. PATENT DOCUMENTS 7,540,716 B2 * 6/2009 Wobben ..................... 416/228
7,543,500 B2 * 6/2009 Litzenberg et al. ............ 73/593
2006/0216153 A1 * 9/2006 Wobben .................. 416/241 A
2009/0068019 A1 * 3/2009 Wobben .................. 416/241 R
2009/0100822 A1 * 4/2009 Osakabe et al. .......... 60/39.281
2009/0120192 A1 * 5/2009 Suzuki et al. ................. 73/623

FOREIGN PATENT DOCUMENTS

| EP | 1906182 A2 | * | 4/2008 |
| JP | 09072501 | * | 9/1995 |
| JP | 02000214136 | * | 4/2000 |
| KR | 10-2006-0008552 |  | 1/2006 |
| WO | WO2008081484 | * | 7/2008 |
| WO | WO2009000793 | * | 12/2008 |

* cited by examiner

*Primary Examiner*—J M Saint Surin
(74) *Attorney, Agent, or Firm*—Kenyon & Kenyon LLP

(57) ABSTRACT

In a nondestructive testing apparatus for testing normality of a blade root in a steam turbine installed in a nuclear plant or a thermal plant, an ultrasonic probe and an encoder can be mounted at the outside by only removing a casing of the steam turbine, without the necessity of withdrawing a turbine rotor, so that an automatic testing can be performed by rotating the steam turbine. Since the testing result can be digitally stored, reliability of the testing is improved. Furthermore, size of the testing apparatus is highly reduced for a tester to conveniently carry and install the testing apparatus alone. As a result, installation time and the whole testing time can be minimized.

2 Claims, 10 Drawing Sheets

NONDESTRUCTIVE TESTING APPARATUS FOR BLADE ROOT OF STEAM TURBINE OF POWER PLANT

FIELD OF THE INVENTION

The present invention relates to a nondestructive testing apparatus for a blade root in a steam turbine, e.g., that converts steam energy, generated from combustion heat of nuclear fuel or fossil fuel in a nuclear plant or a thermal plant, to mechanical rotative energy, the testing apparatus capable of reducing time for an automatic testing of the blade root and improving reliability of the testing.

BACKGROUND INFORMATION

Generally, a steam turbine installed at nuclear plants and thermal plants is used to convert heat energy of steam to mechanical rotative energy, by colliding high-temperature high-pressure steam with blades arranged in radial directions. When normally operating, the steam turbine performs at about 30 to 60 rotations per second. Also, the steam turbine is structured in such a manner that first to third stages are arranged sequentially from the center.

The blades of the steam turbine are not damaged so frequently during power generation. However, once the blades are damaged, the whole facility may be seriously damaged along with stoppage of the power generation operation. Great expenses are incurred to restore the facility. Also, a long repair time is required.

According to statistics regarding power generation, damage of the blades by crack, corrosion, and parts damage occupies about 30% of accidents of the steam turbine. A centrifugal tension generated by rotation of a rotor of the steam turbine and a bending stress generated by influent steam are among the main stresses causing such damages of the blades. Furthermore, vibration at a nozzle inlet caused by unevenness of the influent steam induces continuous fatigue.

In relation to design of the steam turbine, differently from fatigue cracks generated by resonant vibration of the blades, the cracks occurring on the blades are mostly caused by corrosion. Furthermore, such cracks are generated most frequently at a root of the blade, where a body of the steam turbine and the blade are fixed, rather than at the blade.

As illustrated in FIG. 1, a steam turbine may be structured as follows. Blades 110 each having a steam turbine tenon 140 and fixed on a disc 120 are radially arranged through 360 degrees. The discs 120 are arranged in plural stages symmetrically with respect to an axis of a turbine rotor 100. The disc 120 and the blade 130 are interconnected through a blade root 130.

Conventional methods for performing a nondestructive testing of the blade root 130 of the steam turbine can be classified into a manual testing and an automatic testing both using ultrasonic waves. According to the ultrasonic automatic testing, as illustrated in FIG. 2, the turbine rotor 100 is arranged on a roller 141 and rotated by the roller 141, thereby testing the blade root 130. More specifically, a rail 160 is installed parallel with the axis of the turbine rotor 100, and a testing apparatus 150 tests the respective blade roots 130 by moving along the rail 160 in an axial direction of the turbine rotor 100. Referring to FIG. 2, an ultrasonic probe is mounted to an end of a testing arm 170 to obtain signals corresponding to tested parts.

As illustrated in FIG. 3, the testing can be performed remotely by attaching to the turbine 100 a driver 180 which is magnetically driven.

However, the above conventional testing methods are believed to bear various problems as follows and therefore are believed to require certain improvements.

For example, the testing apparatus 150 including the rail 160 weighs much and occupies a large space due to a large volume. Therefore, in a restricted steam turbine room of the power plant, much manpower and equipment are required to operate the system. Especially, since a prop for preventing shaking of the testing apparatus 150 is a kind of heavy goods weighing about 300 kg, it is difficult to handle the testing apparatus 150.

Furthermore, the testing arm 170 for reaching the inside of the steam turbine from the outside is long. Therefore, the ultrasonic probe mounted at the restless end of the testing arm 170 can hardly contact with a tested object by a proper pressure. Furthermore, transmission of ultrasonic energy to the tested object cannot be achieved effectively, thereby deteriorating reliability of the testing.

Moreover, the roller 141 is necessary to rotate the steam turbine at a predetermined speed. In order to test the steam turbine through 360 degrees, a testing apparatus having access to the steam turbine through 360 degrees is required. However, since such a testing apparatus is unavailable, the steam turbine itself needs to be rotated by 360 degrees.

Still further, in order to disassemble, withdraw and transfer the steam turbine to a testing place, significant manpower and time are required. In addition, there exists an operator's risk in handling such a heavy system.

When transferring to a next tested object after completing the test of one steam turbine, reinstallation of the testing apparatus is necessitated, which takes significant time.

SUMMARY

Example embodiments of the present invention provide a nondestructive testing apparatus for a blade root of a steam turbine in a power plant, capable of rotating the steam turbine at a regular speed using a motor attached to the steam turbine to operate the steam turbine with only a steam turbine casing detached instead of with the whole steam turbine withdrawn from an operation place, performing a test from the outside with an ultrasonic probe fixed to a static wing, and performing the test while recording position information by an encoder attached to a predetermined position of the steam turbine and storing ultrasonic signals corresponding to each position, thereby providing carriage of a testing system by minimizing the size of the whole testing system and saving time for the testing of the steam turbine, as well as improving reliability of the test.

A nondestructive testing apparatus for testing a blade root may be divided largely into two parts.

One of the parts is an ultrasonic probe fixing unit for testing the blade of the steam turbine, and the other is an encoder fixing unit for recording a rotation distance of a rotating turbine rotor.

The ultrasonic fixing unit includes a magnetic body having a magnetic body switchably fixed to a fixture supporter, a first steel shaft fixed vertically to its own magnetic body, a second steel shaft connected to the first steel shaft through a first joint and having a three-dimensional degree of freedom to be rotatable and vertically movable, a contacting pressure controller mounted to the second steel shaft to maintain a predetermined pressure between an ultrasonic probe and the blade which is a tested object, and the ultrasonic probe mounted to a leading end of the second steel shaft through the medium of the contacting pressure controller and a second joint to directly contact the turbine rotor which is the tested object.

The encoder fixing unit includes a magnetic body switchably fixed to the fixture supporter, a first steel shaft fixed vertically to its own magnetic body, a second steel shaft connected to the first steel shaft through a first joint and having a three-dimensional degree of freedom to be rotatable and vertically movable, and an encoder mounted to the second steel shaft rotatably to measure a rotation distance of the turbine rotor.

The contacting pressure controller for controlling a pressure between the ultrasonic probe and the blade may include a load cell detecting the pressure transmitted from the ultrasonic probe through the second joint, a driving motor generating a rotative motion using values detected by the load cell, and a motional direction converter converting the rotative motion of the driving motor to a linear motion so as to detect and control the pressure applied to the ultrasonic probe.

Further features and aspects of example embodiments of the present invention are described in more detail below with reference to the appended Figures.

DETAILED DESCRIPTION

Figure 1:
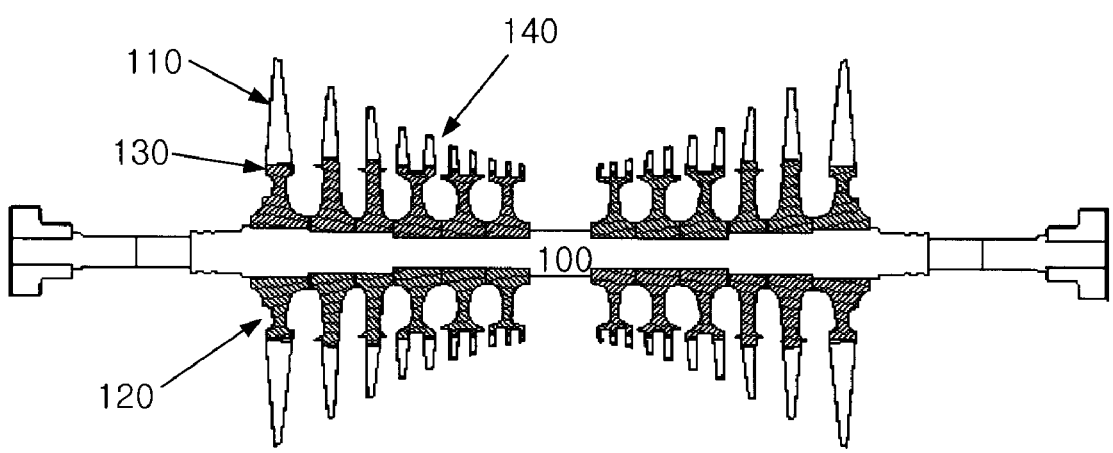
FIG. 1 is a perspective view showing the structure of a steam turbine in a general power plant.
Figure 2:
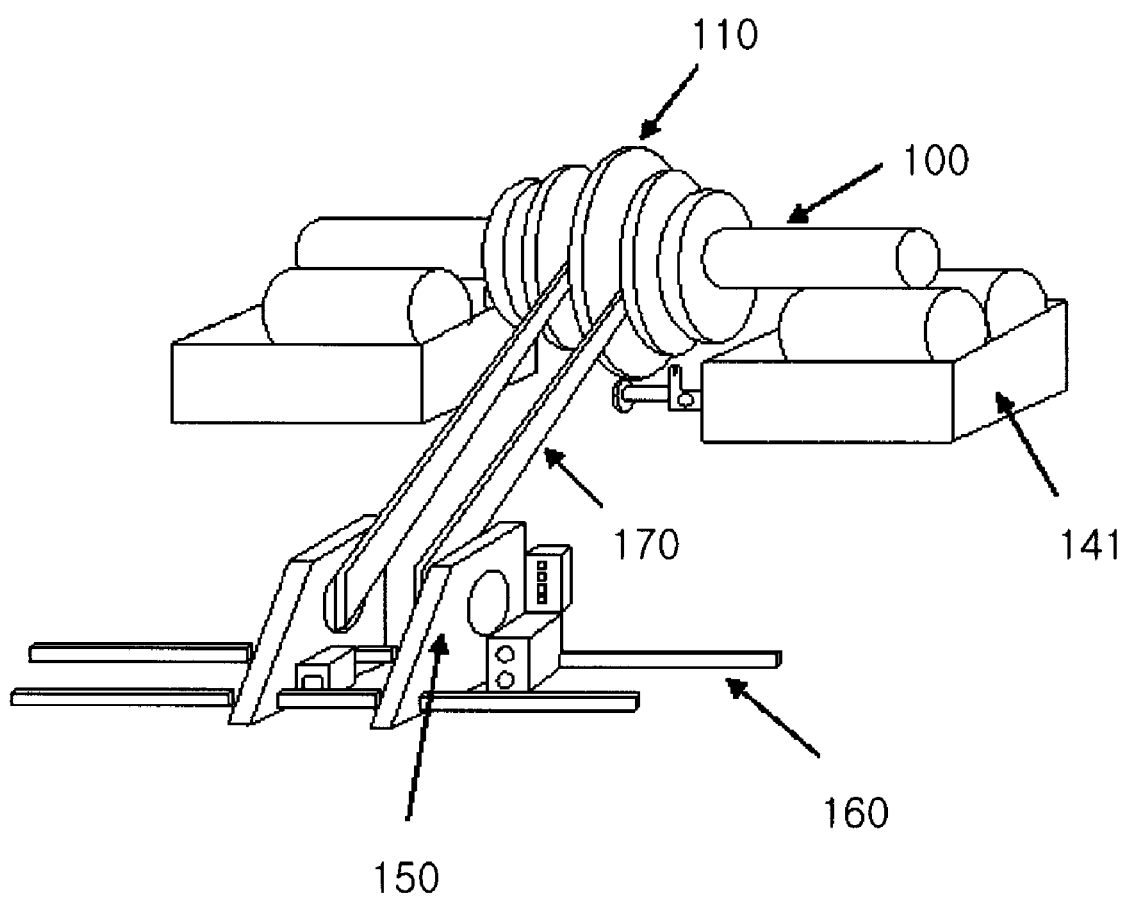
FIG. 2 is a perspective view schematically showing a conventional nondestructive testing apparatus for a blade root of the steam turbine.
Figure 3:
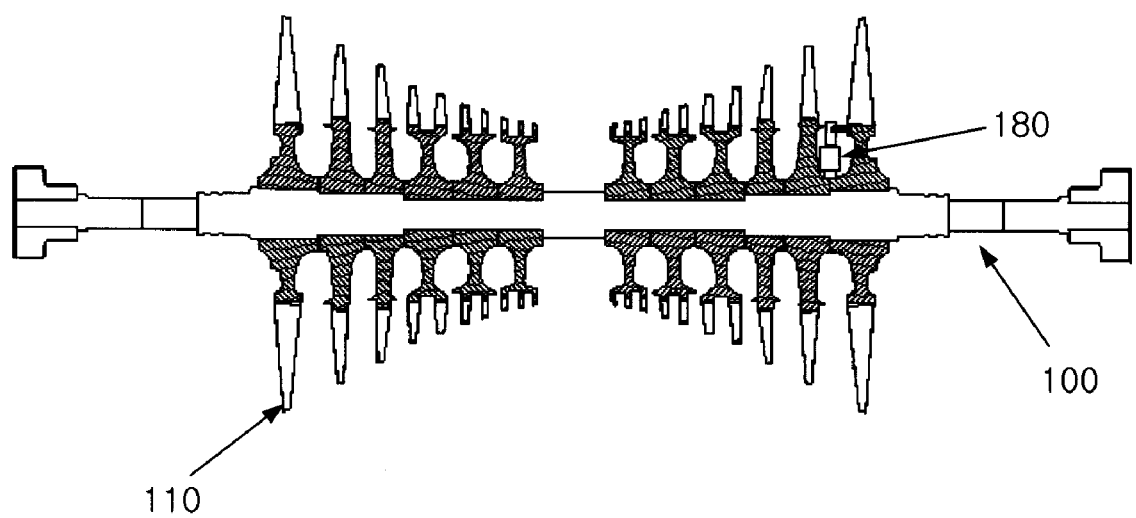
FIG. 3 is a perspective view schematically showing a conventional nondestructive testing apparatus, different from that illustrated in FIG. 2, for a blade root of a steam turbine.

Exemplary embodiments of the present invention are described in more detail with reference to the accompanying drawings.

In the following description, the same or corresponding components as in conventional systems will be provided with the same reference numerals.

Figure 4:
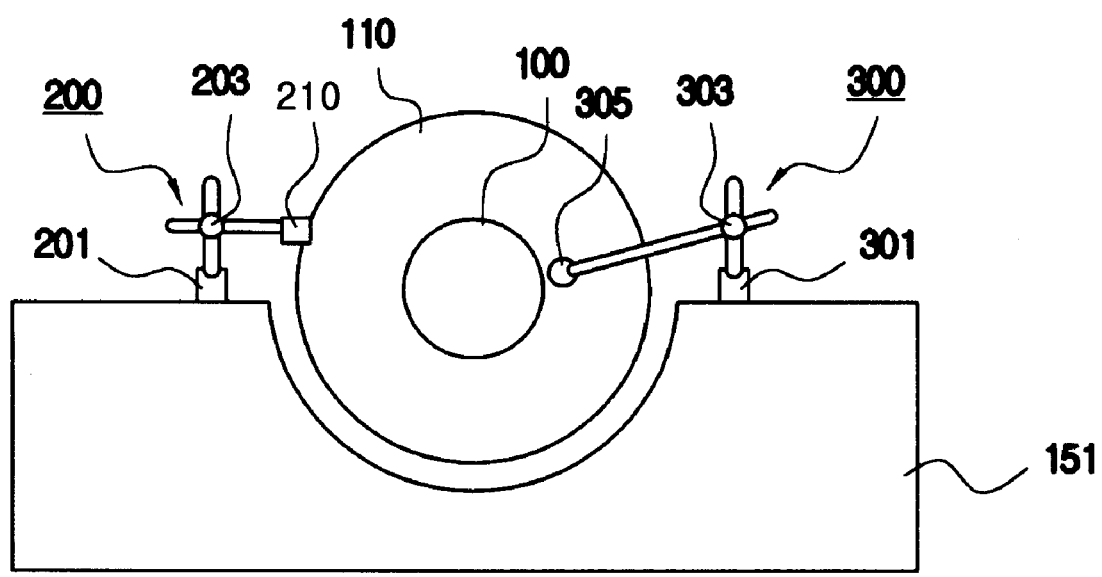
FIG. 4 is a cross-sectional view showing an installation state of a nondestructive testing apparatus for the blade root of the steam turbine, according to an example embodiment of the present invention.
Figure 5:
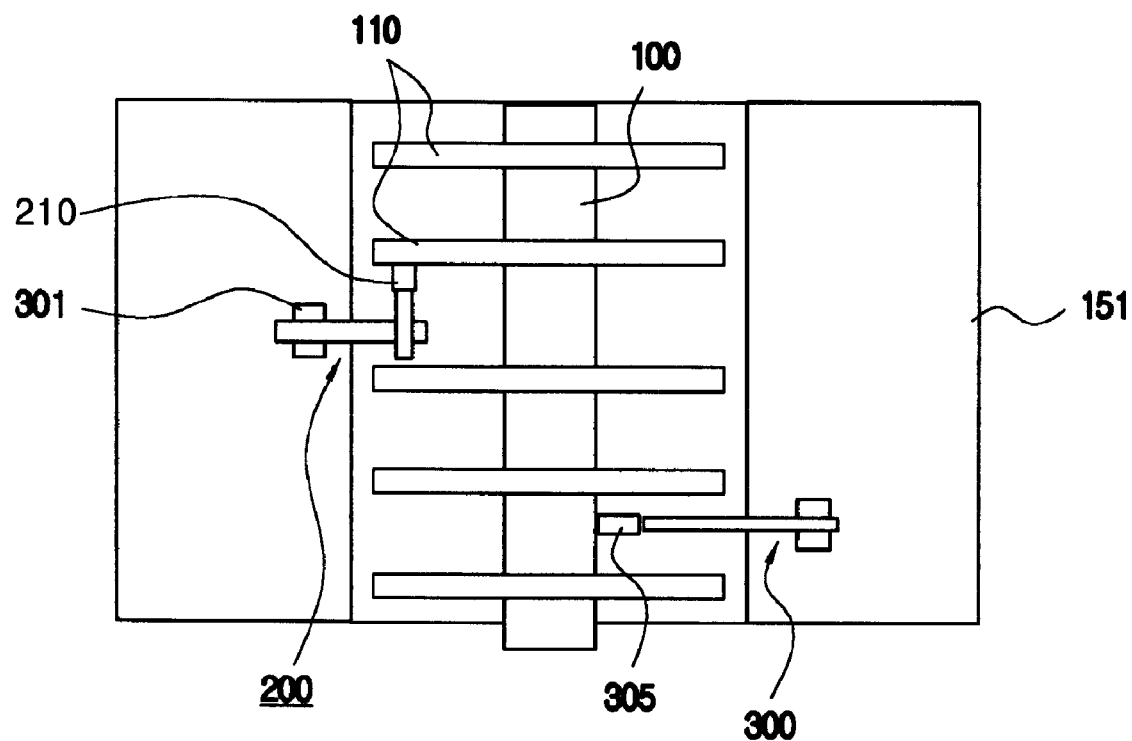
FIG. 5 is a plan view showing an ultrasonic probe fixing unit of FIG. 4 mounted to the steam turbine.

As illustrated in FIGS. 4 and 5, a nondestructive testing apparatus for a blade root of a steam turbine installed in nuclear plants and thermal plants, performing the testing using a probe, includes an ultrasonic probe fixing unit 200 for testing a blade 110 of the steam turbine and an encoder fixing unit 300 for recording a rotation distance of a rotating turbine rotor 100.

Figure 6:
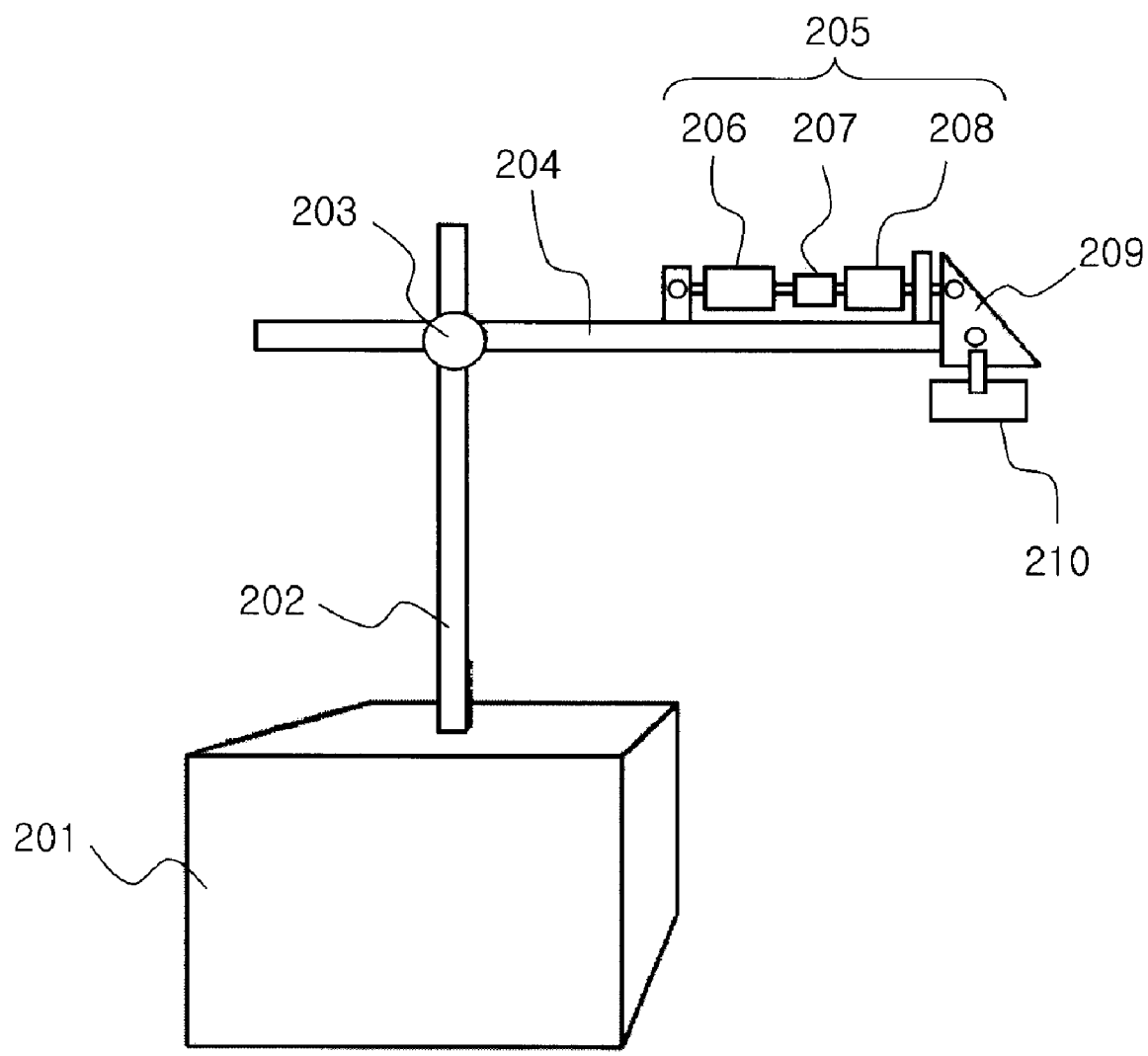
FIG. 6 is a perspective view of the ultrasonic probe fixing unit of the testing apparatus.

Referring to FIG. 4 and FIG. 6, the ultrasonic probe fixing unit 200 includes a magnetic body 201 switchably fixed to a fixture supporter 151, a first steel shaft 202 fixed vertically to its own magnetic body 201, a second steel shaft 204 connected to the first steel shaft 202 through a first joint 203 in a horizontal posture with respect to the figure and having a three-dimensional degree of freedom, that is, rotatable and vertically movable, and a contacting pressure controller 205 including a driving motor 206, a motional direction converter 207 and a load cell 208 that are mounted to the second steel shaft 204 to control a contacting force applied to an ultrasonic probe 210, and the ultrasonic probe 210 connected to a leading end of the second steel shaft 204 through a second joint 209.

Figure 7:
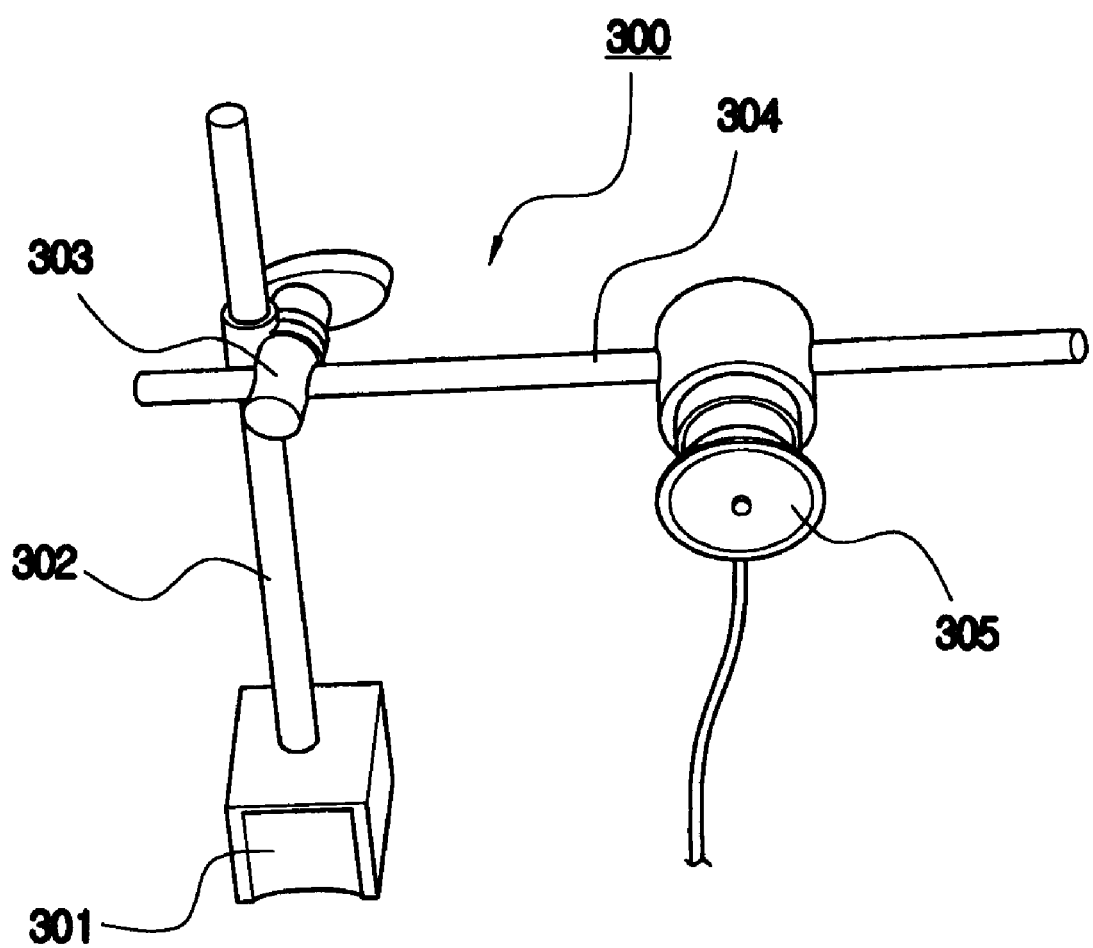
FIG. 7 is a perspective view of an encoder fixing unit of the testing apparatus.

The encoder fixing unit 300, as illustrated in FIG. 5 and FIG. 7, includes a magnetic body 301 switchably fixed to the fixture supporter 151, a first steel shaft 302 vertically fixed to the magnetic body 301, a second steel shaft 304 connected to the first steel shaft 302 through a first joint 303 in a horizontal posture with respect to the figure and having a three-dimensional degree of freedom, that is, rotatable and vertically movable, and an encoder 305 mounted to the second steel shaft 304 to be rotatable by 360 degrees so as to measure the rotation distance of the turbine rotor 100.

In the above-structured ultrasonic probe fixing unit 200, the magnetic body 201 is switchably attached to the fixture supporter 151 and the first steel shaft 202 is fixed to the magnetic body 201 in a vertical posture. Since the second steel shaft 204 is connected to the first steel shaft 202 in a horizontal posture through the first joint 203, the second steel shaft 204 accordingly has a three-dimensional degree of freedom, that is, being movable vertically along the first steel shaft 202 through the first joint 203 and rotatable by 360 degrees. The second steel shaft 204 is equipped with the contacting pressure controller 205 for maintaining a predetermined pressure between the ultrasonic probe 210 and the blade 110 of the steam turbine, which is a tested object. The contacting pressure controller 205 reads a force value of the load cell 208 equal to the pressure transmitted from the ultrasonic probe 210 through the second joint 209, and converts the rotational motion of the driving motor 206 to the linear motion at the motional direction converter 207 by comparing the read value with a preset value of the load cell 208. As the second joint 209 is pushed and pulled by the linear motion, the contacting pressure of the ultrasonic probe 210 is controlled so that the ultrasonic probe 210 can contact to a desired position of the blade 110 of the steam turbine, which is the tested object.

The ultrasonic probe fixing unit 200 is capable of bringing the ultrasonic probe 210 into contact with the blade 110 of the steam turbine without an additional operation in a state where a casing of the steam turbine is opened. When the ultrasonic probe 210 is in contact with the blade 110, the steam turbine is rotated at a regular speed by an operation motor mounted to the steam turbine, thereby providing the testing to be performed omnidirectionally through 360 degrees.

In order to perform the automatic testing, it is necessary to record the rotation distance of the turbine rotor 100. For this purpose, the encoder 305 needs to be attached to a proper position on a body of the steam turbine, to be accessible to the rotating steam turbine at any position. As a device for attaching the encoder 305, the encoder fixing unit 300 illustrated in FIG. 7 may be appropriately applied. The encoder fixing unit 300, while supporting the encoder 300, brings the encoder 305 into contact with the rotating steam turbine by exerting a predetermined force in a desired direction.

In the same manner as the ultrasonic probe fixing unit 200, the encoder fixing unit 300 is also rotatable by 360 degrees by the first steel shaft 302, the second steel shaft 304, and the first joint 303, and therefore is contactable to a desired position as illustrated in FIG. 5.

Figure 8:
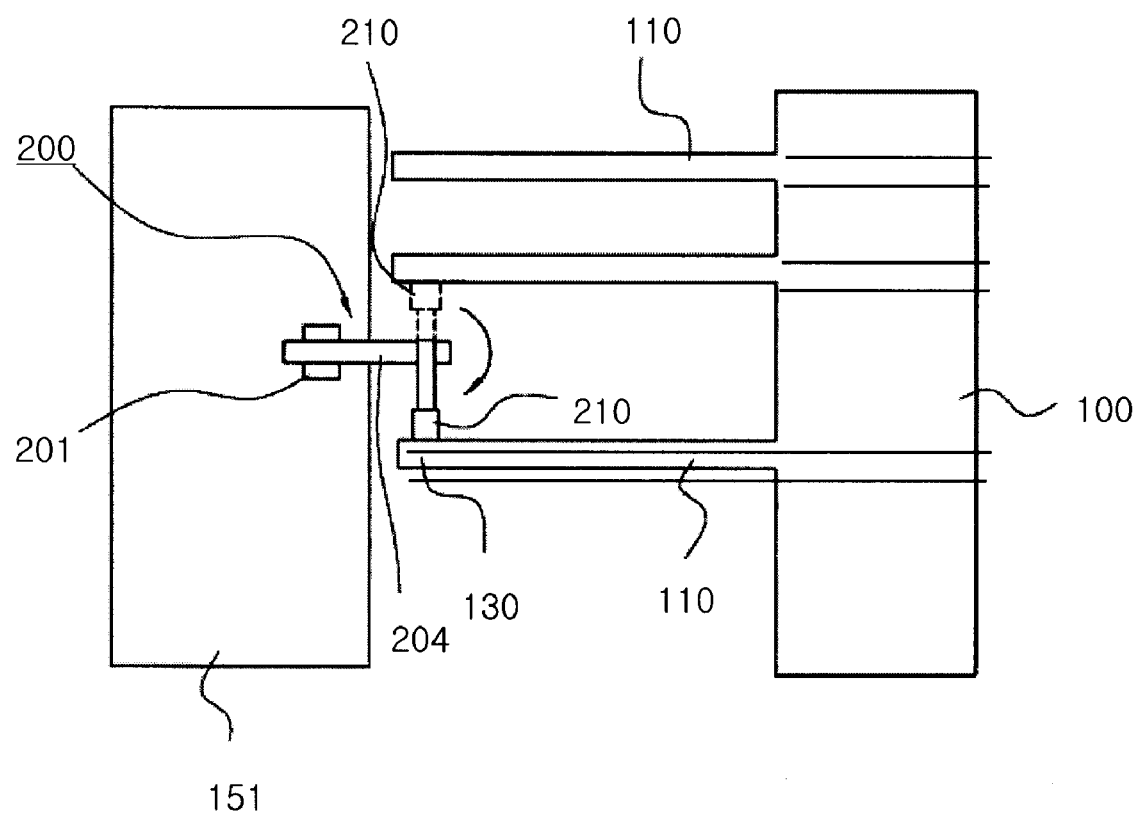
FIG. 8 is a plan view showing the testing apparatus being rotated by 180 degrees to test the blade root nearby.

After the fixture supporter 151 for the ultrasonic probe fixing unit 200 and the encoder fixing unit 300 is mounted, when the testing of one stage is completed, the second joint 204 is rotated by 180 degrees as indicated by an arrow in FIG. 8 to perform testing with an adjoining stage. Therefore, the root 130 of the blade 110 disposed at the opposite side can be tested.

As explained above, the testing apparatus hereof is able to perform testing with the roots 130 of the blades 110 of the discs 120 on both sides at one position. Consequently, the testing time and the manpower can be considerably saved.

Figure 9:
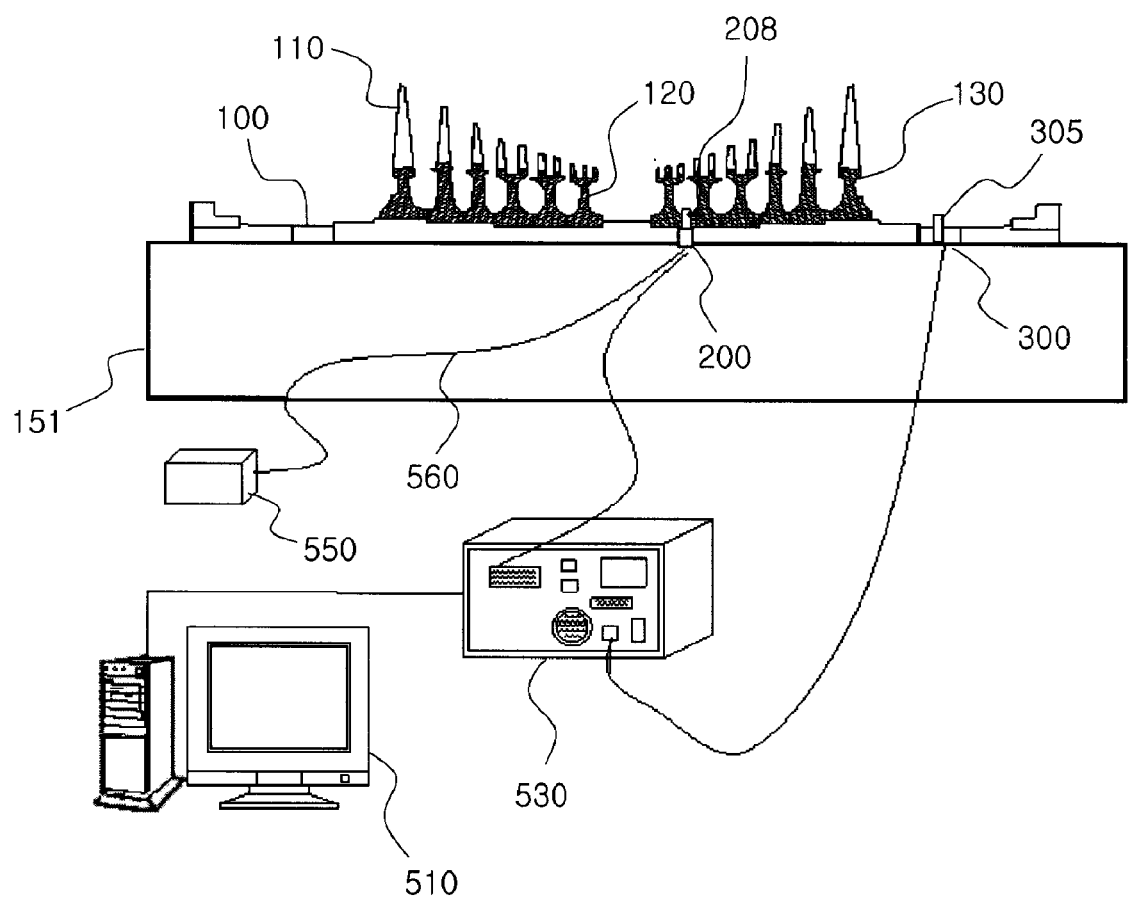
FIG. 9 is a structural view of the whole system for testing the steam turbine using the testing apparatus.
Figure 10:
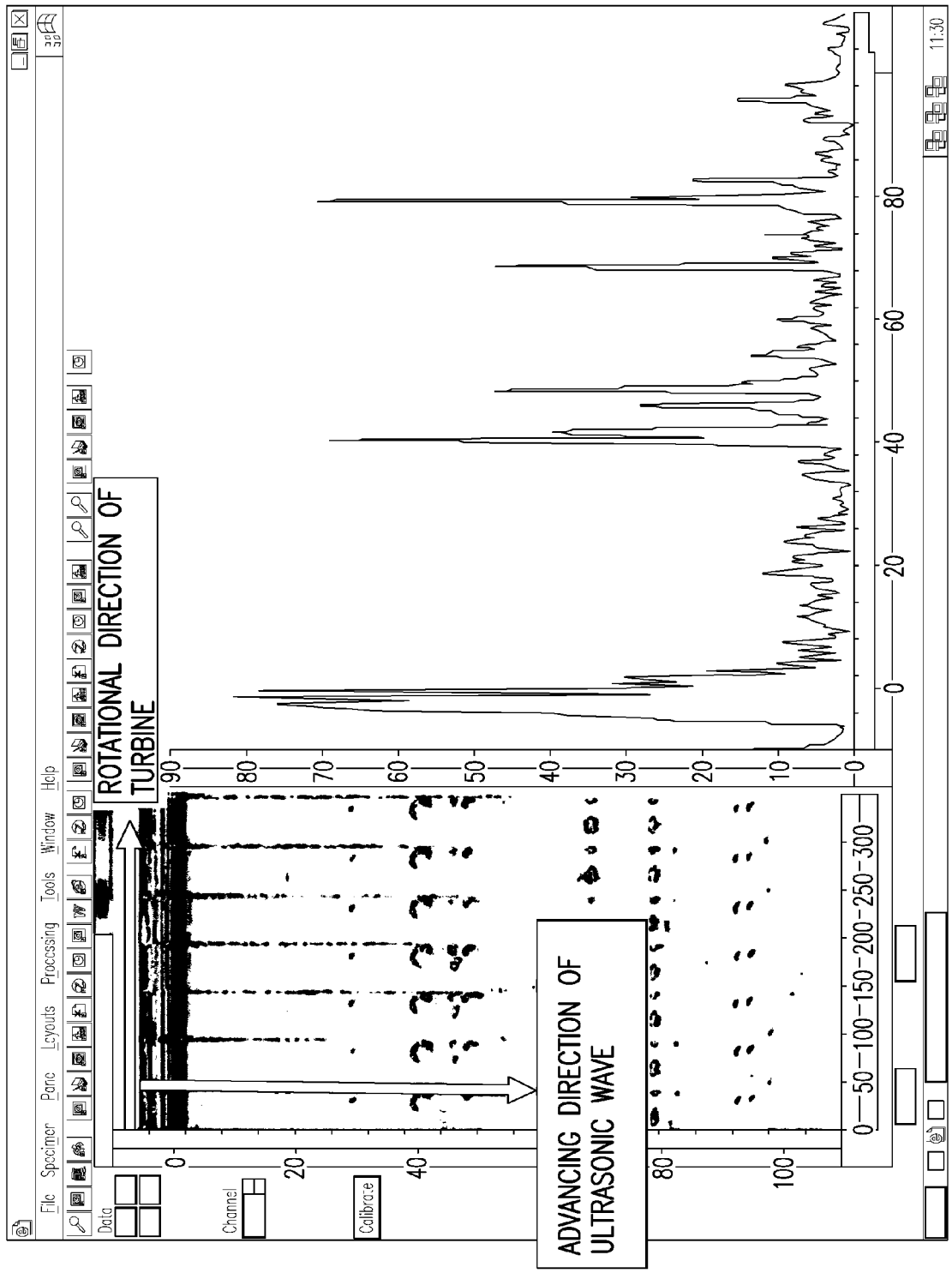
FIG. 10 shows a screen of signal evaluation showing the result of the testing of the steam turbine using the ultrasonic probe and the encoder.

Meanwhile, as illustrated in FIG. 8, an ultrasonic signal from the ultrasonic probe 210 and the rotation distance according to rotation of the turbine rotor 100 are detected by the encoder 305, and received by a general ultrasonic transceiver 530. The received signal is stored in a general personal computer (PC) 510 through a local area network (LAN) to be analyzed and utilized as the result of the testing. FIG. 9 is a graph displaying a state of the ultrasonic nondestructive testing performed on the PC 510 using the ultrasonic probe 210.

In order to perform the ultrasonic nondestructive testing, the ultrasonic probe 210 needs to contact with the tested object through a contacting medium so as to transmit ultrasonic waves to a surface of the tested object. Therefore, a general contacting medium is supplied from an outlet of a contacting medium supplier 550 through a hose 560.

Generally, in order to obtain signals with excellent sensitivity during the ultrasonic nondestructive testing, the ultrasonic probe 210 is required to contact with the surface of the tested object by a predetermined pressure. Accordingly, the load cell 208 and the driving motor 206 are provided at a rear end of the ultrasonic probe 210 such that the ultrasonic probe 210 operates the regular pressure against the disc 120.

When a conventional testing apparatus is used, it takes about 5 to 12 hours for only installing the testing apparatus. However, the testing apparatus hereof demands just 20 to 30 minutes, thus highly saving the installing time. In addition, it takes less than even 10 hours for opening the steam turbine casing, withdrawing the steam turbine and transferring the steam turbine to the testing place as preparation for the testing. Therefore, the time for preparing the testing can be remarkably reduced.

Moreover, when using the conventional testing apparatus, it can take more than an hour to move to the next stage after the testing with one stage. On the contrary, the testing apparatus hereof may require only about 5 minutes to do the same.

To summarize, the testing apparatus according to example embodiments of the present invention is capable of performing a nondestructive testing stably in a simple manner. Furthermore, the time for testing the steam turbine can be greatly reduced.

As should be appreciated from the above description, example embodiments of the present invention may solve various problems occurring when the steam turbine is tested by the conventional testing apparatus. For example, since considerable time is required from withdrawing the steam turbine for the testing to completing the nondestructive testing, a testing term should sometimes be extended during the operation of the power plant. However, the nondestructive testing apparatus according to example embodiments of the present invention effectively saves time for being installed and removed. Reliability of the testing result can be highly enhanced. In addition, it becomes easier to find and evaluate a defect of the testing apparatus.

Although example embodiments of the present invention have been described for illustrative purposes, those skilled in the art should appreciate that various modifications, additions and substitutions are possible, without departing from the scope and spirit of the present invention.

What is claimed is:

1. A nondestructive testing apparatus for testing a blade root of a steam turbine installed in at least one of (a) a nuclear plant and (b) a thermal plant by using an ultrasonic probe, comprising:
    an ultrasonic probe fixing unit configured to test the blade of the steam turbine; and
    an encoder fixing unit configured to record a rotation distance of a rotatable turbine rotor;
    wherein the ultrasonic fixing unit includes a first magnetic body switchably fixed to a fixture supporter, a first steel shaft fixed vertically to the first magnetic body, a second steel shaft connected to the first steel shaft through a first joint and having a three-dimensional degree of freedom to be rotatable and vertically movable, a contacting pressure controller mounted to the second steel shaft configured to maintain a predetermined pressure between the ultrasonic probe and the blade, the ultrasonic probe mounted to a leading end of the second steel shaft by the contacting pressure controller and a second joint to directly contact the turbine rotor; and
    wherein the encoder fixing unit includes a second magnetic body switchably fixed to the fixture supporter, a third steel shaft fixed vertically to the second magnetic body, a fourth steel shaft connected to the third steel shaft by a third joint and having a three-dimensional degree of freedom to be rotatable and vertically movable, and an encoder mounted to the fourth steel shaft rotatably to measure a rotation distance of the turbine rotor.

2. The nondestructive testing apparatus according to claim 1, wherein the contacting pressure controller configured to control a pressure between the ultrasonic probe and the blade includes a load cell configured to detect the pressure transmitted from the ultrasonic probe through the second joint, a driving motor configured to generate a rotative motion using values detected by the load cell, and a motional direction converter configured to convert the rotative motion of the driving motor to a linear motion to detect and control the pressure applied to the ultrasonic probe.

* * * * *